United States Patent [19]

Higuchi et al.

[11] Patent Number: 5,146,102
[45] Date of Patent: Sep. 8, 1992

[54] FINGERPRINT IMAGE INPUT APPARATUS INCLUDING A CYLINDRICAL LENS

[75] Inventors: Yoshinori Higuchi, Yokohama; Jun Hanari, Kawasaki, both of Japan

[73] Assignee: Kabushiki Kaisha Toshiba, Kawasaki, Japan

[21] Appl. No.: 586,215

[22] Filed: Sep. 21, 1990

[30] Foreign Application Priority Data

Feb. 22, 1990 [JP] Japan ................................ 2-39858
Feb. 26, 1990 [JP] Japan ................................ 2-42438

[51] Int. Cl.⁵ .............................................. G06K 5/00
[52] U.S. Cl. .............................. 250/556; 250/227.11; 356/71; 382/4
[58] Field of Search ........... 250/227.11, 227.2, 227.24, 250/556, 227.28; 356/71, 73; 382/4, 5, 2

[56] References Cited

U.S. PATENT DOCUMENTS

| | | | |
|---|---|---|---|
| 3,882,462 | 5/1975 | McMahon | 356/71 |
| 3,968,476 | 7/1976 | McMahon | 382/4 |
| 4,136,332 | 1/1979 | Kadota et al. | 340/146.3 H |
| 4,186,378 | 1/1980 | Moulton | 340/146.3 E |
| 4,208,625 | 6/1980 | Marshall | 382/18 |
| 4,218,673 | 8/1980 | Yoshida | 382/18 |
| 4,310,827 | 1/1982 | Asai | 382/5 |
| 4,322,163 | 3/1982 | Schiller | 356/71 |
| 4,340,300 | 7/1982 | Ruell | 356/71 |
| 4,414,684 | 11/1983 | Blonder | 356/71 |
| 4,441,205 | 4/1984 | Berkin et al. | 382/18 |
| 4,537,484 | 8/1985 | Fowler et al. | 382/4 |
| 4,569,080 | 2/1986 | Schiller | 382/4 |
| 4,573,193 | 2/1986 | Shuto et al. | 382/2 |
| 4,635,293 | 1/1987 | Watanabe | 382/44 |
| 4,688,088 | 8/1987 | Hamazaki et al. | 358/101 |
| 4,728,186 | 3/1988 | Eguchi et al. | 356/71 |
| 4,784,484 | 11/1988 | Jensen | 382/4 |
| 4,805,223 | 2/1989 | Donyer | 382/4 |
| 4,878,248 | 10/1989 | Shya et al. | 382/9 |
| 4,924,085 | 5/1990 | Kato et al. | 250/227.28 |

FOREIGN PATENT DOCUMENTS

| | | | |
|---|---|---|---|
| 4538480 | 12/1970 | Japan . | |
| 54-77499 | 6/1979 | Japan . | |
| 0173688 | 9/1985 | Japan | 382/9 |
| 0175865 | 8/1986 | Japan | 382/2 |
| 1-320586 | 12/1989 | Japan . | |
| 1178258 | 1/1970 | United Kingdom . | |

OTHER PUBLICATIONS

Bishop et al., "Character Recognition Approach Involving H. Stagian Classification," *IBM Technical Disclosure Bulletin*, vol. 21, No. 9, Feb. 1979.

*Primary Examiner*—David C. Nelms
*Assistant Examiner*—John R. Lee
*Attorney, Agent, or Firm*—Oblon, Spivak, McClelland, Maier & Neustadt

[57] ABSTRACT

A fingerprint image input apparatus for optically detecting ridges of a skin surface of a finger and inputting a detected signal to various control units, includes a transparent member having a lower surface and an upper surface on which the finger subjected to fingerprint detection is pressed, a light source for emitting light from said lower surface to said upper surface of said transparent member, a photosensor for detecting light reflected or scattered from said upper surface of said transparent member, and means, inserted midway along an optical path from said light source to said photosensor, for linearly (in a predetermined direction) focusing light incident on said photosensor, wherein the fingerprint input apparatus further includes another transparent member formed so that the upper surface of the transparent member on which the finger is pressed serves as a light scattering plane with respect to a wavelength of the light.

9 Claims, 6 Drawing Sheets

FINGERPRINT IMAGE INPUT APPARATUS INCLUDING A CYLINDRICAL LENS

BACKGROUND OF THE INVENTION

1. Field of the Invention

The present invention relates to a fingerprint image input apparatus for inputting a fingerprint image of a finger surface to a computer or the like.

2. Description of the Related Art

In recent years, along with the development of an information-oriented society, security techniques for personal verification have received a great deal of attention to aim at control of areas as intelligence and security for important areas and access control to computer terminals. A method using an ID card or a password is very popular as a method of verifying a person's identity for a specific person. This system has limited safety, and therefore demand has arisen for developing a more safe system which is easy to operate.

In general, fingerprints have been used to verify person's identity due to its major features, i.e., "unchangeability throughout life" and "no identical patterns", and high verification precision can be obtained. In a conventional method, fingerprint photographs are used to identify fingers, and the photographic patterns are discriminated by human beings. In recent years, however, fingerprints tend to be discriminated and identified by computers due to the development of electronic techniques. For this purpose, image input apparatuses for accurately inputting fingerprint information to computers are required, and many proposals have been made and are being made.

Although various methods have been proposed in conventional fingerprint input apparatus, most popular apparatuses optically detect signals of fingerprint information and processing the fingerprint signals as two-dimensional signals. Another conventional method, such as forming of multi-value projection signals in the longitudinal direction of the finger, is also proposed ("Method of Verifying Person's Identity", Takeda, Uchida, Hiramatsu, and Matsunami, Technical Research Report in Japan the Institute of Electronic and Communication Engineers: PRU 89-50). According to this method, when only one-dimensional signals are used, the data volume can be greatly reduced as compared with a two-dimensional signals of fingerprint image, and a processing algorithm can be simplified. For this reason, a signal processing speed can be increased, and the time required for verifying person's identity can be shortened. This method is rarely affected by ridges of a skin surface of a finger, i.e., finger ridge lines, broken lines, and adhesion. The "fingerprint" in this specification represents the whole or part of ridges on finger skin, which include patterns on the skin surface of the finger as a whole.

Image input apparatuses for optically reading fingerprints are based on the following three methods due to their principles of operation.

The first method is "total reflection method" (Japanese Patent Application No. 42-9347: Fingerprint Verification Apparatus).

The second method is "light-path separation method" (Japanese Patent Application No. 57-26153: Three-Dimensional Pattern Information Detecting Method).

The third method is "scanning method" (Japanese Patent Application No. 53-130600, Fingerprint Processing Apparatus; and Japanese Patent Application No. 56-183189, Method and Apparatus for Processing Fingerprint).

These conventional methods pose the following problems. More specifically, in the first method (total reflection method) or the second method (light-path separation method), an object lens and an image input device are required to accurately receive the fingerprint image. The lens and the image input device (i.e., those elements which constitute an image input device) consequently are generally expensive in cost. In order to form multi-value projection signals in the longitudinal direction of the finger, all data of the entire finger must be input. In order to input all the data of the entire finger in the form of image signals by one operation, a long distance between the object lens and the finger is required because the operation is determined by the image input device and an object lens used together with the image input device.

For example, assume that an image pickup element (having a light-receiving surface of 8.8 mm × 6.6 mm) equivalent to a ⅔ inch element is used as an image input device, and that data of a 50-mm long finger are input using an object lens having a focal length of 16 mm. Under these assumptions, a minimum distance between the object lens and the finger is about 90 mm. When the total size of the object lens and the image input device, that is, the size of the image input apparatus, is also taken into consideration, the fingerprint image input apparatus as a whole is expected to become bulky. This limits easy installation and free transportation of the apparatus.

In the first method, light from a light source incident on an image input apparatus through the object lens is light totally reflected on the surface of a transparent member. This condition is equivalent to a case wherein an observer watches the light source, and the screen is very bright. A fingerprint image obtained by a finger pressed on the surface of the transparent body is obtained by light scattering upon tight contact of the projection surface of the fingerprint with the transparent body. For this reason, when an amount of light reflected by a portion of the fingerprint is decreased, a dark image viewed in the bright field of view has a low contrast level, and minute portions of the fingerprint cannot be easily read.

The surface on which the finger is pressed must be an optically very flat polished surface in order to improve the characteristics of total reflection. Fat and moisture are attached to the surface of the transparent member every time the apparatus is used. When fat and moisture which have refractive indices similar to that of the transparent member are attached to the total reflection surface upon incidence of light, light is not totally reflected at a boundary between the clean surface of the transparent member and a surface portion with a fat and is transmitted through the fat. Since the boundary between the fat and the air is not flat due to the surface tension of the fat, light is reflected or scattered at the boundary between the fat and the air. The fat and moisture on the surface of the finger, which are left and attached to the surface of the transparent member every use emphasizes a dark image of scattered light in the totally reflected bright field of view. This scattered image overlaps the original image obtained upon tight contact between the finger and the surface of the transparent member, thereby further decreasing the contrast level of the original image.

In the second method, a bright image of scattered light is formed in a dark field of view. In principle, since this image is formed by scattered light, an amount of light of the image portion is small and S/N ratio is reduced, but a decrease in contrast as in the first method does not occur in the second method because a portion surrounding the scattered light image is a dark field of view. However, since light incident on the image input apparatus is limited to light scattered by the ridges of the skin surface of a finger, the resultant image is susceptible to a change in ambient brightness. When fat is left on the transparent surface which totally reflects light from a light source, an image formed by scattered light appears as in the first method. Upon reflection, the scattered light does not reach the image input apparatus. The light is transmitted through the fat without being totally reflected at the boundary between the transparent member and the fat, and light reaches the boundary surface between the fat and the air. Since the boundary surface between the fat and the air is not a flat surface due to the surface tension of the fat, the total reflection condition cannot be satisfied, and light is reflected by an amount which is determined by a difference of refractive indices of the air and the fat. The reflected components are incident again on the transparent member from different directions. Some components reach the image input apparatus. An image formed by these components overlaps the true fingerprint image and becomes noise against the true fingerprint image.

Since the third method (scanning method) is a method of mechanically scanning a light beam, an optical system and a mechanical system are required to focus a beam into a beam spot. These systems are optically and mechanically complicated. Alternatively, a special light source such as a laser for focusing light into a small beam spot and an expensive lens almost free from aberration must be used. In addition, it takes a long period of time to receive signals.

Even if any one of the first to third methods is employed, a common problem is presented. That is, a multi-value projection image (i.e., a signal having ridge information representing different shapes) must be formed from the two-dimensional image signals of the entire finger. This processing requires a lot of information to form image signals of the entire finger. A complicated processing algorithm is required to process signals so as to obtain a multi-value projection signal. As a result, it takes much time to perform the above signal processing.

As described above, many problems described above are posed by the conventional methods. A multi-value projection signal in the longitudinal direction of the finger is formed from the image signals of the entire finger. The one-dimensional signals are extracted as finger characteristics, i.e., as signals for verifying person's identity. This method requires a large amount of data to obtain the image signals of the entire finger, and the complicated algorithm is required to perform signal processing to obtain a multi-value projection signal from the image signals. It takes a long period of time to perform signal processing.

In order to input the image signals of the entire finger by one operation, a long distance between the object lens and the finger is required due to the limitations of the image input devices and the object lens. As a result, the apparatus as a whole becomes bulky.

The conventional apparatuses for inputting finger images (i.e., apparatuses based on the first and second methods) has a low contrast level or a low S/N ratio due to the residual fat.

The third method requires a special light source such as a laser which can be focused to form a very small beam spot and an expensive lens almost free from aberration. As a result, the structure is complicated at high cost.

SUMMARY OF THE INVENTION

It is an object of the present invention to provide a simple, low-cost fingerprint image input apparatus capable of inputting a one-dimensional signal consisting of multi-value projection signals in the longitudinal direction of a finger within a short period of time, and preventing decreases in contrast level and S/N ratio caused by a residual fat.

According to the present invention, two-dimensional signals of a finger as a whole are formed and processed (electrical additions) not to form the multi-value projection signal (fingerprint information), but to form one-dimensional fingerprint information by optical additions.

In order to achieve the above object of the present invention, there is provided a fingerprint image input apparatus for optically detecting ridges on a skin surface of a finger and inputting a detected signal to various control units, comprising a transparent member having an upper surface on which a finger subjected to fingerprint detection is pressed, a light source for emitting light from a lower surface to the upper surface of the transparent member, a photosensor for detecting light reflected or scattered by the upper surface of the transparent member, and means, inserted midway along an optical path from the light source to the photosensor, for linearly focusing light incident on the photosensor. In other words, a linear or one-dimensional image is formed, with the light optically synthesized such that the two-dimensional image information is synthesized into a one-dimensional feature, or is linearly focused, in a direction perpendicular to the longitudinal direction of the object (i.e., finger) to obtain a one-dimensional representation of the two-dimensional information.

In order to achieve the above object of the present invention, there is provided a fingerprint input apparatus comprising a transparent member, means for illuminating light from a lower surface to an upper surface of the transparent member, and means for detecting light reflected by the surfaces of the transparent member, so that a fingerprint image of a surface of a finger pressed on the upper surface of the transparent member is input as an image signal through the transparent member, wherein, of the upper surface of the transparent member, at least an upper surface portion which contact the finger is formed as a light scattering plane with respect to a wavelength of the light.

According to the present invention, the light emitted from a light source illuminates a transparent member surface on which the finger is pressed. On the surface which contacts the finger, the light is scattered by ridges of a skin surface of the finger and is reflected by recesses on the skin surface. The reflected light contains ridge/recess information as light intensity information. In this case, the fingerprint image signal as two-dimensional information can be obtained from the reflected light. When the reflected light is linearly focused (i.e., the two-dimensional input image information is optically synthesized or added together in a direction perpendicular to the longitudinal direction of the object to obtain a one-dimensional information feature) by an optical element (i.e., focusing means) such as a cylindrical lens in the longitudinal direction of the finger, the signals (one-dimensional fingerprint information) have been optically added in a direction of width of the finger.

The direction of the linearly focused beam obtained by the above technique corresponds to the longitudinal direction of the finger. A joint near the fingertip is called the "first joint", and a joint near the root of the finger is called the "second joint". Data of the "first joint", the "second joint", and the "root of the finger" are linearly aligned with finger wrinkle information. The widthwise direction of the linearly focused beam is the widthwise direction of finger wrinkles. When focused beam information is photoelectrically transferred i the longitudinal direction, a sum signal along the widthwise direction of the finger can be obtained.

In order to perform such photoelectric transfer, a one-dimensional sensor having a large number of photoelectric transducer elements aligned in a line may be used. The resolution of the one-dimensional sensor in the longitudinal direction is required enough to sufficiently detect finger wrinkle information in the longitudinal direction of the linearly focused beam.

When a pitch of a fingerprint, i.e., a pitch between ridges is generally about 0.5 mm, enlargement or reduction is not performed along the longitudinal direction of the linearly focused beam. If a signal having the same pitch as described above is assumed, a necessary resolution of the one-dimensional photosensor is at least 0.5 mm.

When enlargement or reduction is performed in the longitudinal direction of the linearly focused beam, a necessary resolution of the one-dimensional photosensor is decreased or increased as compared with the case described above. The "size" and "width" of the one-dimensional photosensor in the longitudinal direction must allow photoelectric transfer of the linearly focused beam containing finger information enough to provide signals necessary for person's identity. The value of the resolution is determined by magnifications in the longitudinal and widthwise directions of the linearly focused beam.

In this one-dimensional photosensor, the photoelectric transducer elements sequentially detect information of the linearly focused beam at a given point as electrical signals in the longitudinal direction of the linearly focused beam. When the width-wise direction of each photoelectric transducer element is taken into consideration, the information in the width-wise direction is detected as information at the given point without being decomposed into components. This indicates an electrical addition of the finger wrinkle information in the widthwise direction of the finger. The optical additions and the electrical additions are not distinguished from each other when an image is projected in one direction to form a one-dimensional signal from two-dimensionally formed image information. Procedures for adding proper data must be determined to cope with an application purpose in accordance with optical elements, a light source, cost, and the like.

The optical addition of finger information is performed as described above. That is, fingerprint data are electrically added by the one-dimensional photosensor having one-dimensionally aligned photoelectric transducer elements, and fingerprint information signals as electrical signals are obtained. When the fingerprint information signals as the two-dimensional image information are then added to obtain a one-dimensional signal. These series of operations can be performed more easily than those as described above so as to obtain an identical one-dimensional signal.

When light is incident on a transparent member having a three-dimensional pattern on its surface, this geometrical pattern on the surface causes light scattering, and the reflectance of light can be expressed as a function of surface roughness. A reflectance $R_S$ within the range of $\sigma < \lambda$ is given as follows:

$$R_S = R_0 \exp[-(4\pi\sigma)2/\lambda 2]$$

where $\sigma$ is the square average root of the surface roughness of the transparent member, $\lambda$ is the wavelength, and $R_0$ is the reflectance of a perfectly smooth flat surface.

That is, when the surface of the transparent member has a surface roughness value sufficiently larger than the light wavelength, light incident on the surface of the transparent member is scattered, and this surface serves as a light scanning surface of the incident light.

Part of the scattered light focused by a lens or the like and reaches the image input apparatus. Assume that a finger is pressed on the surface of the transparent member. The ridges of the skin surface of the finger are kept in tight contact with the surface of the transparent member. In a fingerprint portion, the three-dimensional pattern of the surface of the transparent member is filled with the fat on the surface of the finger. A refractive index of glass or a plastic material frequently serving as an optical material is generally about 1.5 to 1.8 (1.5 for optical glass BK-7 described above), and a refractive index of water or a fat is generally about 1.3 to 1.5. Since the refractive index of the fat on the skin surface of the finger is close to the refractive index of the transparent member, the reflectance of the light is decreased at the boundary between the transparent member and the fat on the skin surface of the finger when light is incident from the lower surface to the upper surface of the transparent member. This portion equivalently becomes a light scattering surface or plane, and light from the light source is scattered. A fingerprint image is formed on the upper surface of the transparent member in the scattered light when the image is viewed from the lower surface.

Assume that the finger is separated from the light scattering surface. Part of the fat filled in the three-dimensional pattern on the upper surface of the transparent member is left thereon. Its amount is very small and cannot fill the entire pattern formed on the upper surface of the transparent member. Only a small amount of fat is left in the recesses on the upper surface of the transparent member. Light incident from the lower surface of the transparent member and reaching its upper surface is transmitted through the residual fat. Since the three-dimensional pattern is present at the boundary surface between the residual fat and air, light is similarly scattered and cannot be distinguished from surrounding light components. That is, an amount of fingerprint image left on the upper surface is small.

Additional object and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
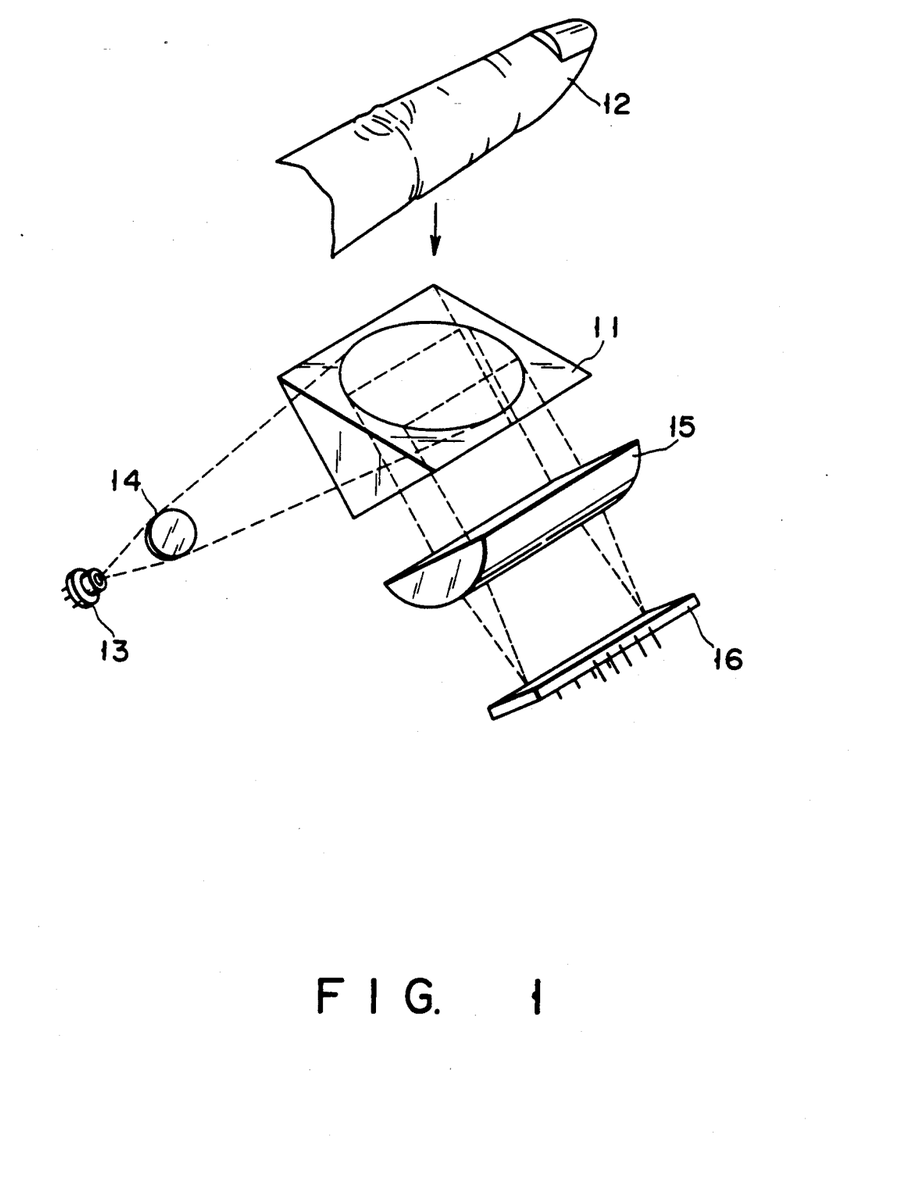
FIG. 1 is a schematic view showing a fingerprint image input apparatus according to an embodiment of the present invention.

As is readily apparent from the description, one feature of the above-mentioned embodiment resides in the use of the cylindrical lens 15 shown in FIG. 1. This cylindrical lens 15 provides a one-dimensional data feature, or in other words can be characterized as a one-dimensional feature data generator, which optically synthesizes two-dimensional image information of a finger in a direction perpendicular to the longitudinal direction of the finger, to generate the one-dimensional feature information. More simply put, the cylindrical lens 15 serves as a dimension converter.

Reference numeral 11 in FIG. 1 is a transparent member having an upper surface on which a finger 12 subjected to fingerprint detection is pressed. The transparent member 11 comprises a prism. Reference numeral 13 denotes a light source. Light emitted from the light source 13 is focused by a condenser lens 14 to obtain a collimated light beam. The upper surface of the transparent member 11 on which the finger 12 is pressed is illuminated from the lower surface of the transparent member 11. Light reflected by the upper surface of the transparent member 11 is linearly focused (i.e., the two-dimensional input information is synthesized or added in a direction perpendicular to the longitudinal direction of the object to provide information in the form of a one-dimensional feature) by a cylindrical lens 15 and is received by a photosensor 16. Although not shown, a detection output (signal) from the photosensor 16 is input to a computer or the like and is collated with preregistered fingerprint information.

Optical glass such as BK-7 is generally used as a material for the transparent member 11. A plastic material such as PMMA may be used in place of glass. When a plastic material is used as a material for the transparent member, it is effective to form a hard thin film on the surface of the plastic member, so as to increase the hardness of the upper surface. The size of the surface of the transparent member 11 which contacts the transparent member 11 is enough to obtain signals for person's identity. Similarly, the light which is required to illuminate the surface of the transparent member 11 which contacts the finger must have a magnitude enough to obtain signals for person's identity.

The light source 13 may be an incandescent lamp, a light-emitting diode, or a laser. The incandescent lamp or light-emitting diode is used to uniformly illuminate a surface without using a condenser lens. The laser is used in combination with a condenser lens when a sufficient light amount cannot be obtained by other light sources. When compactness and energy saving of the apparatus are taken into consideration it is most effective to use a semiconductor laser.

When the upper surface of the transparent member 11 is illuminated from its lower surface, light is scattered at a portion where the ridges of the skin surface of the finger are in tight contact with the upper surface of the transparent member. Light is reflected at the recesses of the skin surface of the finger. The reflected light contains the skin surface ridge/recess information as light intensity information. The reflected light is linearly focused by the cylindrical lens 15 and reaches the photosensor 16. In this embodiment, the direction of the beam linearly focused by the cylindrical lens 15 corresponds to the longitudinal direction of the finger. Data of the first joint, the second joint, and the root of the finger, and the finger wrinkle data are contained as the light intensity information. More specifically, a recess of the skin surface of the fingertip or wrinkles at a joint portion are not brought into tight contact with the upper surface of the transparent member 11 so as to provide a high light intensity, while the ridge or projection of the skin surface of the fingertip or a ridge of a wrinkle between the joints is brought into tight contact with the upper surface of the transparent member 11 so as to provide a low light intensity.

In this embodiment, the widthwise direction of the linearly focused beam corresponds to the widthwise direction of the finger. The length and width of the linearly focused beam can be arbitrarily set within an allowable range enough to obtain signals required for person's identity in accordance with types of the light source 13, the photosensor 16, the condenser lens 14, and the cylindrical lens 15. For example, fingerprints generally vary depending on individuals, and a pitch of ridges of the skin surface of any finger falls within the range of about 0.4 to 0.6 mm. A resolution for detecting these ridges is 0.4 mm or more and preferably about 0.1 mm.

For example, in image projection of the finger 12 to be detected on the photosensor 16, when enlargement or reduction is not performed in the longitudinal direction of the finger 12, i.e., one-to-one size projection is performed, the photosensor 16 must have a resolution of about 0.1 mm. When enlargement or reduction is performed, a corresponding resolution is required. Any sensor may be used as the photosensor 16 if an electrical signal corresponding to a light intensity is obtained and a sufficient resolution can be obtained without losing position information in the longitudinal direction of the linearly focused beam. For example, a sensor capable of sequentially detecting signals from small light-receiving elements arranged in a one-dimensional form (linear), i.e., a photodiode array can be used to obtain a compact, energy-saving apparatus. For this purpose, an element complying with a CCD linear image sensor TCD140AC (specifications: size of each light-receiving element, 14 $\mu$m$\times$14 $\mu$m; total number of elements, 5,000; size of light-receiving portion, 70 mm$\times$14 $\mu$m; and pitch, 14 $\mu$m) available from TOSHIBA CORP. can be used. When this element is used, the optical elements, i.e., the light source 13, the condenser lens 14, and the cylindrical lens 15 must be set so that the range of the linearly focused beam containing signals necessary for person's identity is smaller than all the light-receiving elements.

For descriptive convenience, one condenser lens 14 and one cylindrical lens 15 are illustrated. If the same function as described above can be obtained, the condenser lens 14 and the cylindrical lens 15 may be integrally formed, or one or a plurality of lenses may be used. The type of lens is not limited to the cylindrical lens. A nonspherical lens or a holographic optical element may be used in place of the cylindrical lens. An element having a long light-receiving surface in the widthwise direction of the finger can be effectively used and can be exemplified as a PCD linear image sensor S2304 Series (specifications: size of one light-receiving element, 25 μm×2.5 mm; total element number, 1,024; size of light-receiving portion, 25.6 mm×2.5 mm; and pitch, 25 μm) available from Hamamatsu Photonics Corp. That is, since light need not be focused as a linear spot having a very small width during signal detection, the optical elements for focusing light can be simply designed.

Like this PCD linear image sensor S2304 Series one-dimensional sensor, when a finger to be detected is shorter than 50 mm, e.g., 25.6 mm, light reflected by the transparent member must be focused, i.e., reduced. For example, even when an image of a finger is reduced into ½ in the longitudinal direction of the finger, a required resolution can be obtained, thus posing no problems. A reduction factor can be set to be a proper value in accordance with a length of each light-receiving element of a photosensor and its resolution. An additional optical element may be added in focusing or reduction in the longitudinal direction of the finger. Alternatively, the condenser lens 14, the cylindrical lens 15, or the transparent member 11 may have the same function as described above.

The optical addition in the widthwise direction of the finger have been described above.

The electrical addition will be described below.

The electrical addition is not performed by a signal processing circuit but by each light-receiving element in a one-dimensional sensor. An amount to be added is determined by a width of an optical element. When the width of each light-receiving element is equal to or larger than the width of the finger, optical data need not be focused, i.e., the light reflected by the prism and containing finger information need not be focused in the widthwise direction of the finger. That is, focusing in the widthwise direction of the finger, i.e., the reduction factor can be set to be an appropriate value in accordance with the width of each light-receiving element of the photosensor.

The linear image can perform high-speed driving. It takes about 5 ms for outputs from 5,000 elements at a reference frequency of 1 MHz, or 2.5 ms if a high-speed drive is used. It generally takes about 16 ms for a one-frame output operation of a two-dimensional image input elements if a vertical sync frequency is 60 Hz. When further conversion to a one-dimensional signal is performed, it takes about 50 ms to extract one signal. Therefore, by using the linear image sensor described above, signal processing time can be shortened.

A rectangular prism having a sectional shape of a rectangular equilateral triangle is used as the transparent member 11 in this embodiment. As shown in FIG. 1, since an optical axis of illumination light is perpendicular to a prism incident surface, the advantages of the present invention are not adversely affected by aberrations arising from the use of the prism. When the optical axis is inclined, or a prism having another shape, or parallel flat plates are used, an optical element for correcting the aberration may be added. The aberrations arising from the optical elements employed in the present invention do not adversely affect the accuracy of the identification of a person.

According to this embodiment described above, the light is incident on the upper surface of the transparent member 11 which contacts the finger 12. The light is linearly focused by the cylindrical lens 15 in one direction and is detected by the one-dimensional photosensor 16. In this case, a signal detected by the photosensor 16 is equivalent to a signal (multi-value projection signal) obtained by two-dimensionally detecting a fingerprint image of the finger 12 and electrically adding the resultant signals. Therefore, the one-dimensional signal consisting of multi-value projection signals along the longitudinal direction of the finger 12 can be input within a short period of time. In addition, a circuit for performing electrical signal processing (adding) of two-dimensional signals need not be used, thus simplifying the circuit arrangement.

As compared with a two-dimensional photosensor, the one-dimensional photosensor requires a smaller size and a smaller lens, thus further reducing the overall size of the apparatus.

Other embodiments respectively shown in FIGS. 2 to 6 according to the present invention will be described below. In the embodiment shown in FIG. 2, a cylindrical lens 15 is not arranged on the detection side, but is located on the side where an upper surface of a transparent member 11 which contacts the finger is illuminated. In this case, light reflected by the transparent member 11 is linearly focused on the photosensor 16, thereby obtaining the same effect as in FIG. 1.

Figure 2:
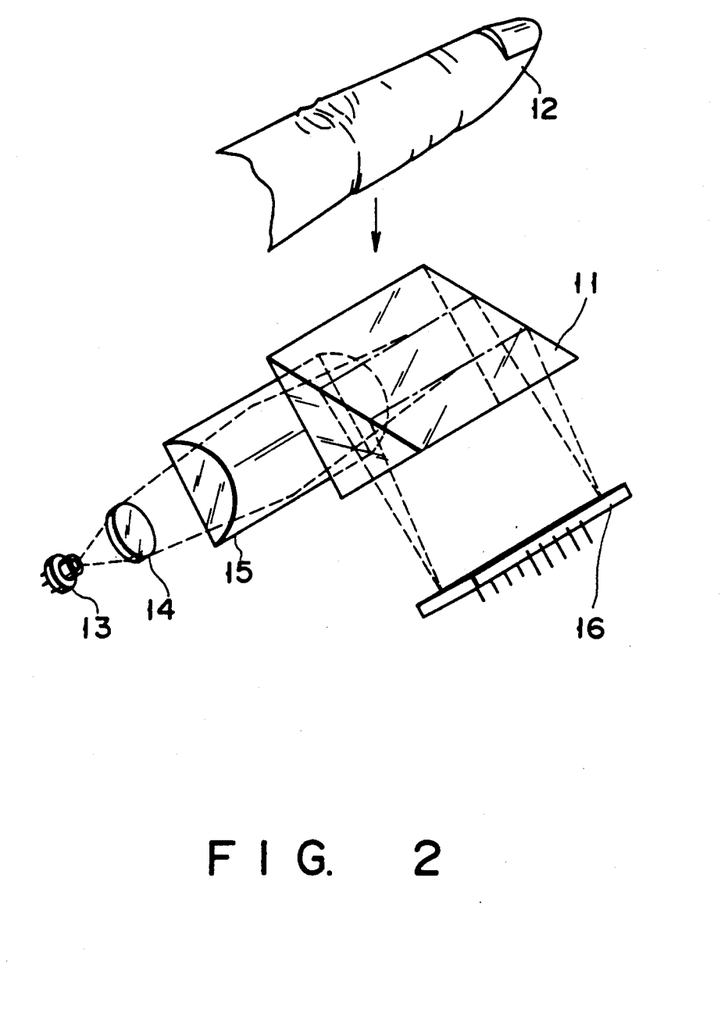
FIGS. 2 to 6 are views showing other embodiments, respectively.
Figure 3:
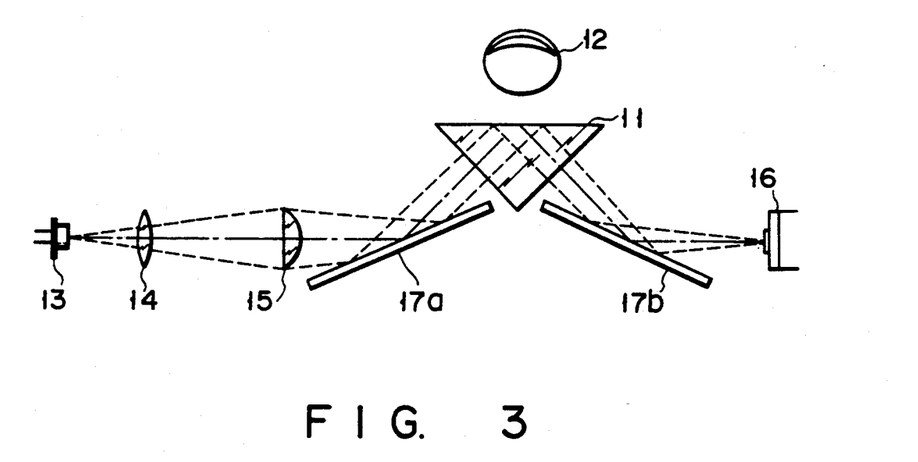

In the embodiment of FIG. 3, mirrors 17a and 17b are located on the light incident and reflection sides, respectively, in addition to the arrangement shown in FIG. 2. In the arrangement of FIG. 3, a low-profile apparatus can be obtained. Note that a cylindrical lens 15 may be arranged on the detection side, as shown in FIG. 1.

Figure 4:
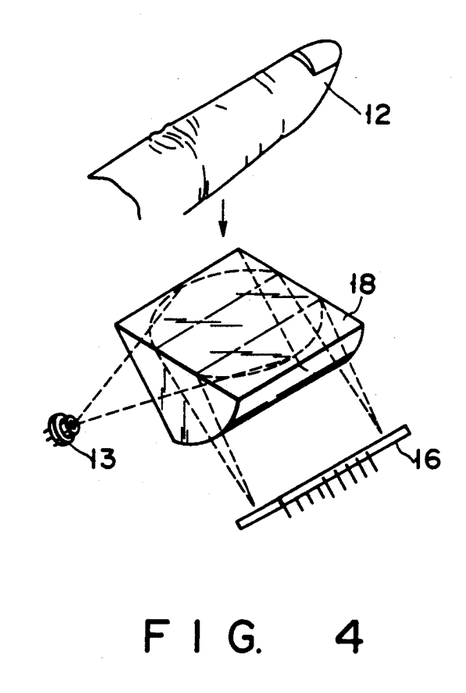

In each of the embodiments shown in FIGS. 1 to 3, an optical element (lens) for focusing an image independently of a transparent member such as a prism is used. A composite optical element integrally including such a lens may be used in place of the above arrangement. As shown in FIG. 4, for example, a composite optical element 18 obtained by integrally forming a cylindrical lens with a prism serving as a transparent member may be used to reduce the number of components of the apparatus.

Figure 5:
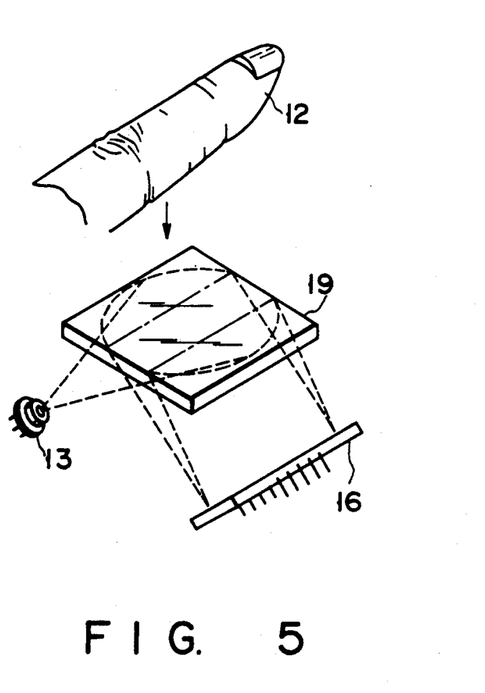

As shown in FIG. 5, the transparent member may comprise a functional component such as a grating lens 19 or a holographic lens. In this case, the apparatus can further be made compact. The grating lens 19 may comprise a lens obtained by forming light-shielding stripes on the lower surface of the transparent member, or a lens having stripe-like layers having different refractive indices inside the transparent member.

Figure 6:
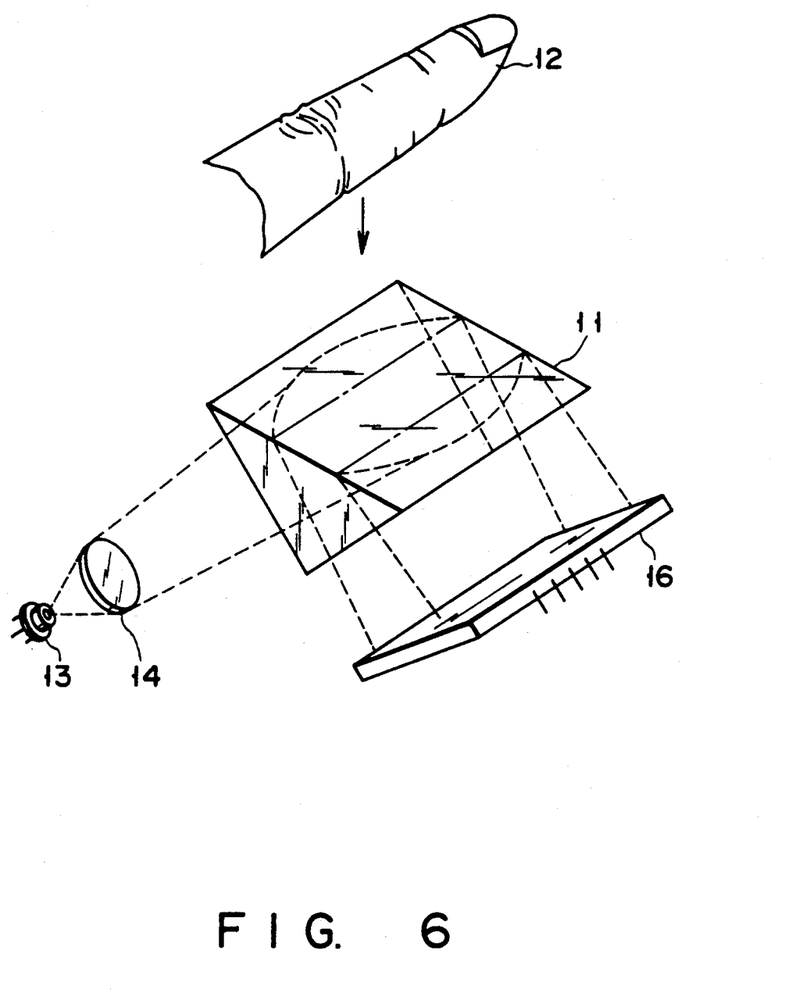

In the embodiment shown in FIG. 6, the cylindrical lens 15 shown in the embodiment of FIG. 1 is omitted. The width of a one-dimensional photosensor 16 in a direction perpendicular to the longitudinal direction of the finger is sufficiently large. For example, the one-dimensional photosensor 16 comprises a sensor (e.g., size of light-receiving element, 100 μm×25 mm; total number of elements, 750; size of total light-receiving portion, 75 mm×25 mm; and pitch, 0.1 mm) which does not require optical additions of information to detect fingerprint information. In this case, light need not be focused by the cylindrical lens 15 or the like. Since widthwise information of the fingerprint is incident on the photosensor 16, the same effect as in the embodiment of FIG. 1 can be obtained. In this embodiment, light is a beam collimated by the condenser lens 14. A projection magnification of light incident from the finger to each light-receiving element is a substantially one-to-one magnification. However, when the size of each light-receiving element is appropriately set, it is possible to use a light source such as a semiconductor laser or a light-emitting diode which emits divergent light.

The present invention is not limited to the particular embodiments described above. In each embodiment described above, the entire part of each finger is subjected to fingerprint detection. However, if coarse detection for person's identity is allowed, only part of a finger may be detected. However, if strict precision for person's identity is required, the entire finger may preferably be detected.

The photosensor need not always be one-dimensionally (linearly) arranged. A few linear photodiode arrays may be grouped (i.e., planar arrangement). In this case, outputs from sensors corresponding to a plurality of lines must be added. However, its signal processing is simpler than that of a general two-dimensional sensor.

In this embodiment, the direction of information addition is the same as the "widthwise direction of the finger". However, the direction of information addition is not limited to this, and can be arbitrarily changed in accordance with technical specifications. For example, the direction of information addition may be slightly inclined from the widthwise direction of the finger or may be the same as the "longitudinal direction of the finger".

The present invention provides an apparatus basically used for detecting fingerprint information, but is also applicable broadly in recognition of a three-dimensional pattern such as a fingerprint.

Various changes and modifications may be made without departing the spirit and scope of the invention.

Still another embodiment will be described below.

Figure 7:
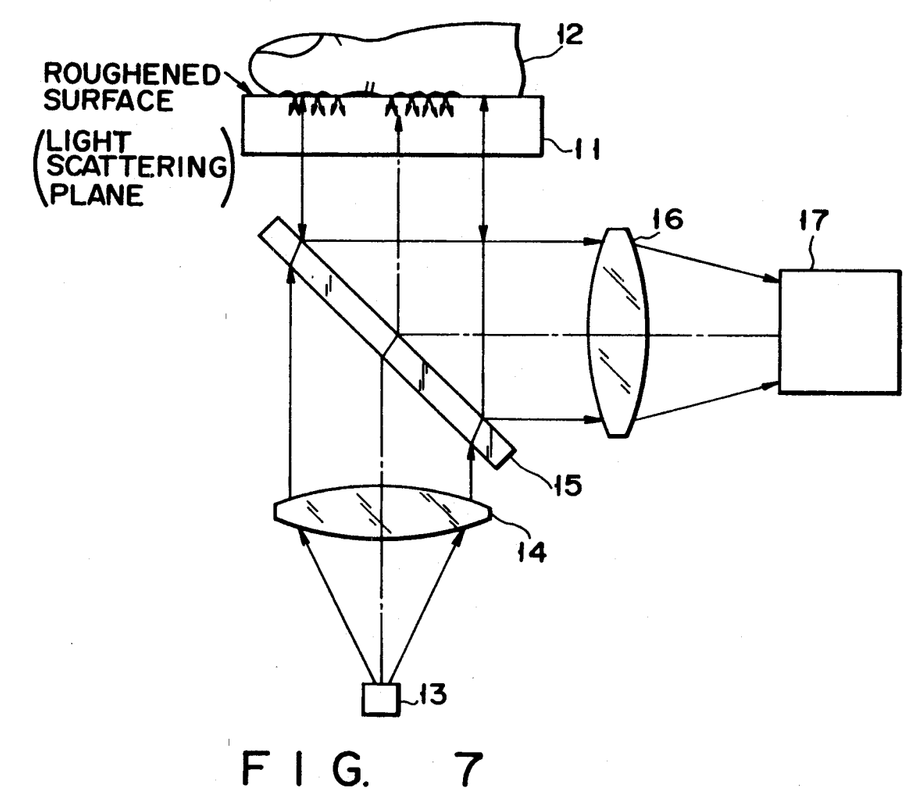
FIG. 7 is a schematic view showing a fingerprint image input apparatus according to still another embodiment of the present invention.

Reference numeral 11 in FIG. 7 denotes a transparent member, an upper surface of which is brought into contact with a finger 12 whose fingerprint pattern is to be detected. A three-dimensional pattern is formed on the upper surface of the transparent member 11. Reference numeral 13 denotes a light source. Light emitted from the light source 13 is focused by a condenser lens 14 to obtain collimated light. This light passes through a beam splitter 15. This light illuminates, from the inside of the transparent member, the three-dimensional pattern of the upper surface of the transparent member 11 on which the finger 12 is pressed. When the three-dimensional pattern on the upper surface of the transparent member 11 is larger than the wavelength of light, the incident light is scattered. Part of the scattered light is reflected by the beam splitter 15 and is focused by a lens 16. The focused image reaches an image input device 17. At this time, at a portion where ridges of the skin surface of the finger are in tight contact with the surface of the transparent member, the three-dimensional pattern of the transparent member 11 is filled with the fat o the skin surface of the finger. When the refractive index of the fat on the skin surface of the finger is close to that of the material of the transparent member, the reflectance of the light at the boundary between the ridges of the skin surface of the finger and the upper surface of the transparent member is reduced. Therefore, the contact portion of the light scattering plane is equivalently transparent.

Optical glass such as BK-7 is generally used as a material of the transparent member 11. In order to form a three-dimensional pattern on the upper surface of the glass plate to obtain a light scattering plane, sandblasting is performed by spraying fine sand particles having a uniform size to roughen the surface, sand particles are brought into fricative contact with the glass surface, chemical etching using a chemical such as hydrofluoric acid is performed, or ion etching for causing ion particles to bombard against the glass surface is performed to roughen the surface. By using either method, a three-dimensional pattern which is several times to several tens of times of the wavelength of visible light can be easily formed.

The image input device 17 comprises an image pickup tube (e.g., a camera tube) or a solid-state image device such as a CCD. In order to obtain a highly reliable, compact apparatus, the solid-state image device such as a CCD is preferably used to obtain an advantageous arrangement. Although not illustrated, an output signal from the image input device 17 is a signal input to a computer or the like. The light source 12 may be an incandescent lamp, a light-emitting diode, a laser, or the like. Of these light sources, the incandescent lamp or the light-emitting diode can be used to uniformly illuminate the surface without using a condenser lens. On the other hand, the laser is used in combination with a condenser lens when a sufficient light intensity cannot be obtained by other light sources.

According to this embodiment, when the finger is pressed on the surface of the transparent member 11 which serves as a light scattering plane formed by roughening of the surface, the upper surface of the transparent member 11 is illustrated from the lower surface of the transparent member 11. Upon detection of the light scattered light from the upper surface, a fingerprint image emphasized on the light scattered image can be obtained. At the same time, unlike in a conventional "scanning method", a fingerprint image can be obtained by a simple structure without using a laser or an expensive lens. As compared with a conventional "total reflection method" and a "light-path separation method", an influence of the residual fat attached to the upper surface of the transparent member can be reduced, and decreases in image contrast level and S/N ratio can be prevented.

Figure 8:
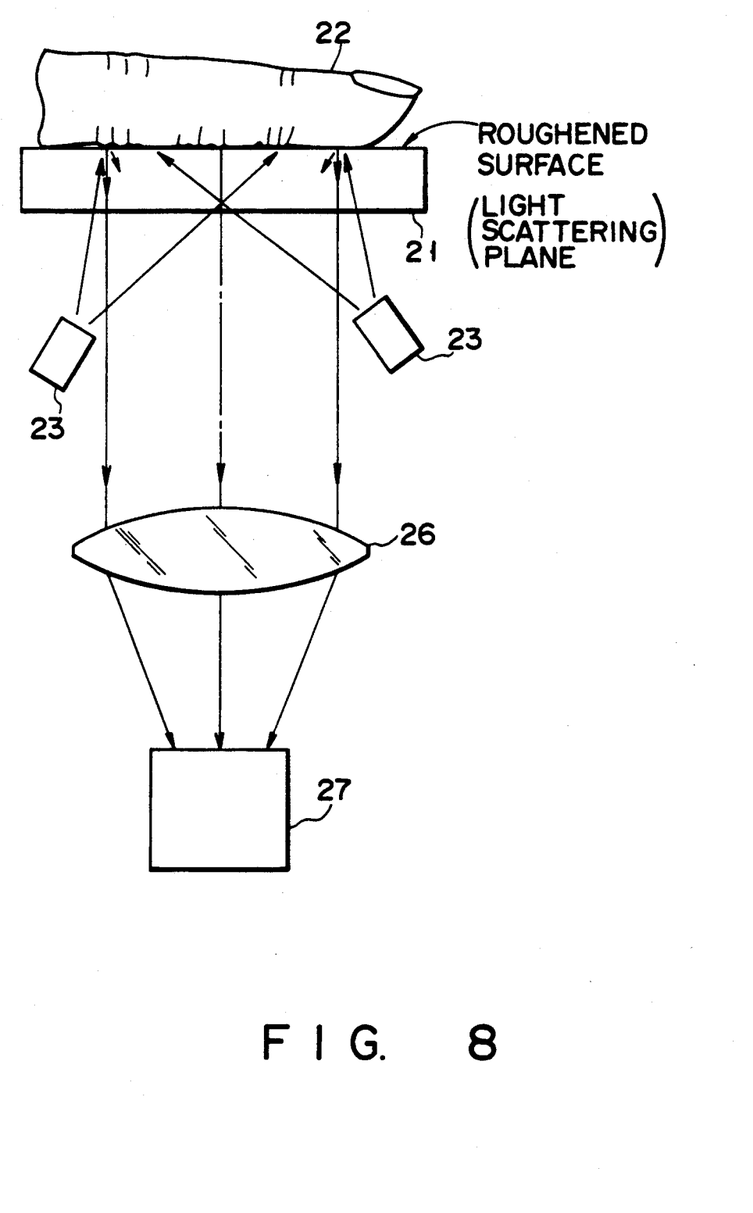
FIG. 8 is a schematic view showing still another embodiment of the present invention.

Reference numerals 21 to 27 in FIG. 8 correspond to reference numerals 11 to 17 in FIG. 7, respectively.

The embodiment of FIG. 8 is substantially the same as that of FIG. 7, except that a light source 23 comprises a light-emitting diode array. When the array of a plurality of light sources is used, the light amount distribution within the irradiated surface can become uniform, and correction for uniforming the amplitude of a signal need not be performed. In the above embodiment, the condenser lens or the beam splitter is arranged between the light source and the transparent member. However, in the embodiment of FIG. 8, elements such as a condenser lens and a beam splitter can be omitted.

The present invention is not limited to the particular embodiments described above. In each embodiment of FIG. 7 or 8, a two-dimensional sensor such as an image pickup tube or a CCD as an image input device is used. However, a line sensor may be used in place of the two-dimensional sensor and may be scanned to obtain a fingerprint image. A plastic material such as PMMA ca be used as a material of the transparent member in place of glass. In this case, injection molding, casting or the like can be used in place of sandblasting. Molding or casting is advantageous since a lot of transparent members can be formed within a short period of time by one mold or die, so that the manufacturing cost can be reduced. Since the three-dimensional pattern of the mold can be accurately reproduced, variations in performance can be expected to be reduced. When a plastic material is used as a material of the transparent member, a hard thin film can be effectively formed on the surface of the transparent member so as to increase the hardness of the upper surface.

Various changes and modifications may be made without departing the spirit and scope of the invention.

According to the present invention as has been described in detail above, light reflected from the upper surface of the transparent member on which the finger is pressed is focused in one direction, and the focused light is detected by the photosensor. Complicated signal processing need not be performed, and one-dimensional fingerprint information can be obtained by optical additions. Therefore there is provided a simple fingerprint image input apparatus wherein the one-dimensional signal constituted by the multi-value projection signals can be input in the longitudinal direction of the finger within the short period of time and wherein the manufacturing cost can be reduced.

Since there is provided the method of obtaining the upper surface of the transparent member as the light scattering plane and obtaining a fingerprint image from a difference between the reflected and scattered light amounts input to the detector upon pressing of the finger on the upper surface of the transparent member, a simple fingerprint image input apparatus capable of prevention decreases in contrast level and S/N ratio caused by the residual fat and decreasing the manufacturing cost can be obtained.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A fingerprint image input apparatus for optically detecting ridges of a skin surface of a finger and inputting a detected signal to various control units, comprising:
   a transparent member having a lower surface and an upper surface on which the finger subjected to fingerprint detection is pressed;
   a light source for emitting light from said lower surface to said upper surface of said transparent member;
   a photosensor for detecting light reflected or scattered from said upper surface of said transparent member; and
   a focusing means, inserted midway along an optical path from said light source to said photosensor, for linearly focusing light incident on said photosensor.

2. An apparatus according to claim 1, wherein said photosensor comprises a one-dimensional sensor constituted by single light-receiving elements consisting of a plurality of small cells linearly arranged in a longitudinal direction of the finger, each of said cells being formed so that a length thereof in a direction perpendicular to a cell alignment direction is larger than that in the cell alignment direction.

3. An apparatus according to claim 2, wherein said photosensor comprises a line sensor which is scanned in a widthwise direction of the finger to obtain a fingerprint image.

4. An apparatus according to claim 1, wherein said focusing means focuses light from said transparent member in a direction perpendicular to the longitudinal direction of the finger.

5. An apparatus according to claim 1, wherein said photosensor comprises at least one photodiode array.

6. An apparatus according to claim 1, wherein said transparent member comprises a composite optical element having a prism function and integrally formed with a cylindrical lens.

7. An apparatus according to claim 1, wherein said transparent member comprises an optical function component such as a grating lens having a lower surface with light-shielding stripes, or a holographic lens having inner stripe-like layers having different refractive indices.

8. An apparatus according to claim 1, wherein said light source comprises at least one of a light-emitting diode for uniformly illustrating a surface and a semiconductor laser for generating divergent light, and a condenser lens.

9. An apparatus according to claim 1, wherein the focusing means optically synthesizes:
   two-dimensional image information in a direction perpendicular to the longitudinal direction of the finger to provide one-dimensional feature information.

* * * * *